(12) United States Patent
Kensey

(10) Patent No.: US 6,497,669 B1
(45) Date of Patent: Dec. 24, 2002

(54) NON-BIOHAZARD BLOOD LETTING SYSTEM

(75) Inventor: Kenneth Kensey, Malvern, PA (US)

(73) Assignee: Rheologics, Inc., Exton, PA (US)

( * ) Notice: Subject to any disclaimer, the term of this patent is extended or adjusted under 35 U.S.C. 154(b) by 0 days.

(21) Appl. No.: 09/873,520

(22) Filed: Jun. 4, 2001

(51) Int. Cl.⁷ .............................................. A61B 5/00
(52) U.S. Cl. ...................................... 600/573; 604/403
(58) Field of Search ................................ 600/573, 576, 600/578, 579, 580, 583; 604/128, 129, 133, 179, 319, 404, 408, 409, 403

(56) References Cited

U.S. PATENT DOCUMENTS

| | | | | |
|---|---|---|---|---|
| 3,654,924 A | * | 4/1972 | Wilson et al. | 128/214 |
| 4,981,474 A | * | 1/1991 | Bopp et al. | 600/580 |
| 5,304,164 A | * | 4/1994 | Lindsay | 604/403 |
| 5,445,629 A | * | 8/1995 | Debrauwere et al. | 604/403 |
| 5,945,004 A | * | 8/1999 | Ohira et al. | 210/710 |
| 6,258,066 B1 | * | 7/2001 | Urich | 604/174 |

* cited by examiner

Primary Examiner—Max Hindenburg

(57) ABSTRACT

An apparatus that allows a patient to blood let safely and automatically and which allows for the safe disposal of the withdrawn blood. The apparatus utilizes an intubator that couples to a blood vessel, a blood collector which contains a micro-biological inactivating agent and a blood conveyor which is coupled between the intubator and the blood collector for passing blood from the intubator to the blood collector.

29 Claims, 4 Drawing Sheets

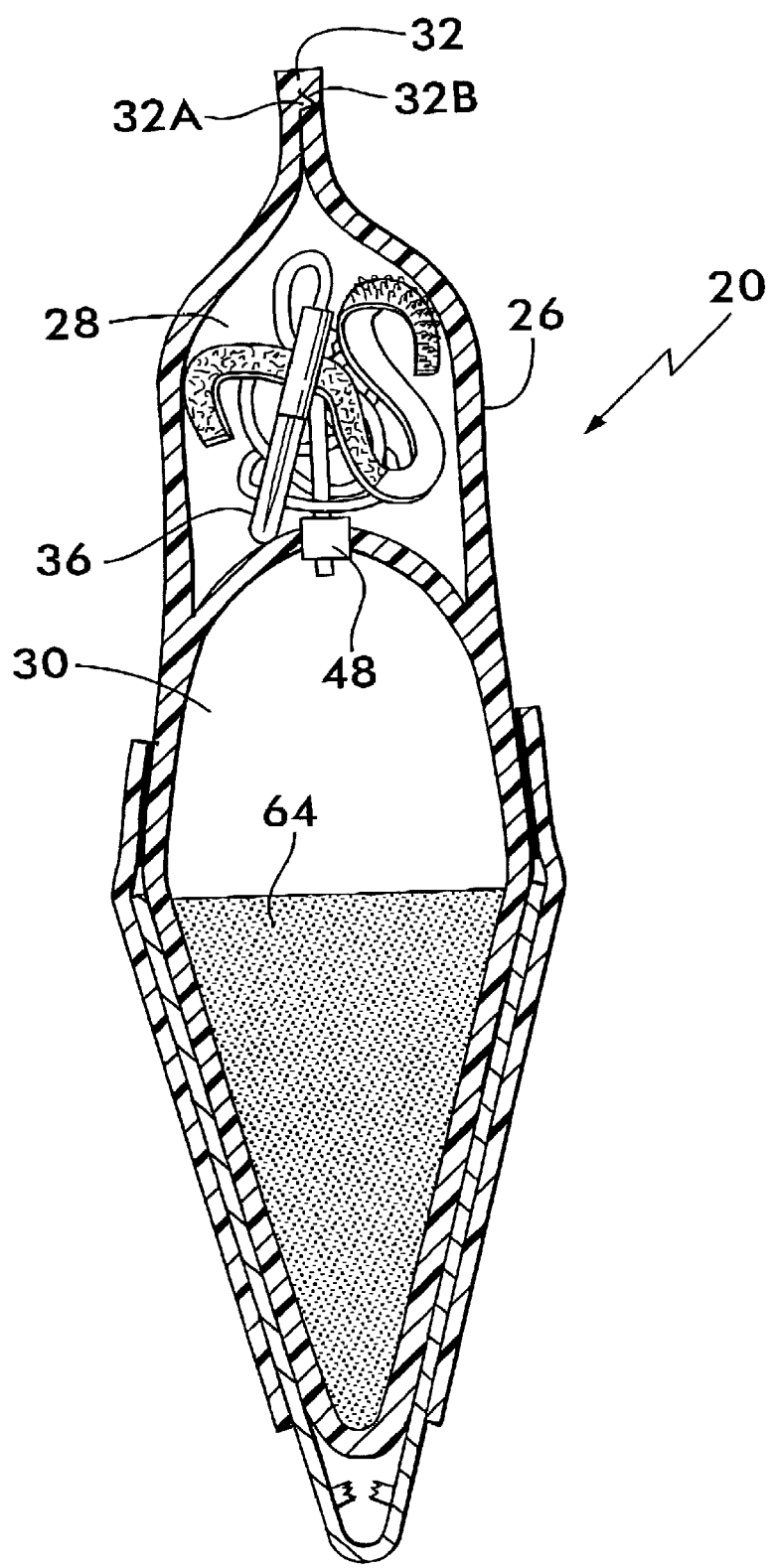

NON-BIOHAZARD BLOOD LETTING SYSTEM

FIELD OF THE INVENTION

The invention pertains to methods and apparatus for reducing blood viscosity of living beings, and more particularly, to methods and apparatus for the automatic and safe removal of blood from a living being.

BACKGROUND OF INVENTION

The concept of removal of blood from a living being, also known as blood letting, has been known for centuries.

However, the particular physiological benefits of removing blood from a living being, and thereby allowing new blood to be created, has not been appreciated in the medical community. For example, a healthy menstruating female removes "old blood" from her body on a monthly basis that is replenished with "fresh blood." A male, on the other hand, does not experience such a cycle and his circulatory system re-circulates "old blood."

Therefore, there remains a need to provide an individual with the ability to safely and automatically blood let while providing a safe and non-biohazardous way of disposing of the removed blood.

SUMMARY OF THE INVENTION

An apparatus for permitting automatic, self-blood letting of a living being of a predetermined amount of blood (e.g., approximately 1 pint) and which renders the removed blood non-biohazardous (e.g., using an internal micro-biological inactivating agent) for safe disposal.

A method of permitting automatic, self-blood letting of a living being of a predetermined amount of blood while rendering the removed blood non-biohazardous for safe disposal. The method comprises: (a) providing a blood collector that normally has an expanded state and which contains a micro-biological inactivating agent (e.g.,bromine, chlorine, Methylene blue (MB) and its derivatives azure A, B, C and thionine); (b) evacuating the blood collector of atmospheric pressure to form a compressed state of the blood collector; (c) coupling a releasable biasing member to the blood collector to maintain the blood collector in the compressed state until a desired time; (d) coupling the blood vessel of the living being to the blood collector; (e) activating the releasable biasing member to cause the blood collector to rapidly expand to draw the predetermined amount of blood into the blood collector; (f) de-coupling the blood collector from the blood vessel; and (g) discarding the blood collector.

DESCRIPTION OF THE DRAWINGS

FIG. 3 is a cross-sectional view of the blood letting system of the present invention that is ready for safe disposal.

DETAILED DESCRIPTION OF THE PREFERRED EMBODIMENTS

Figure 1:
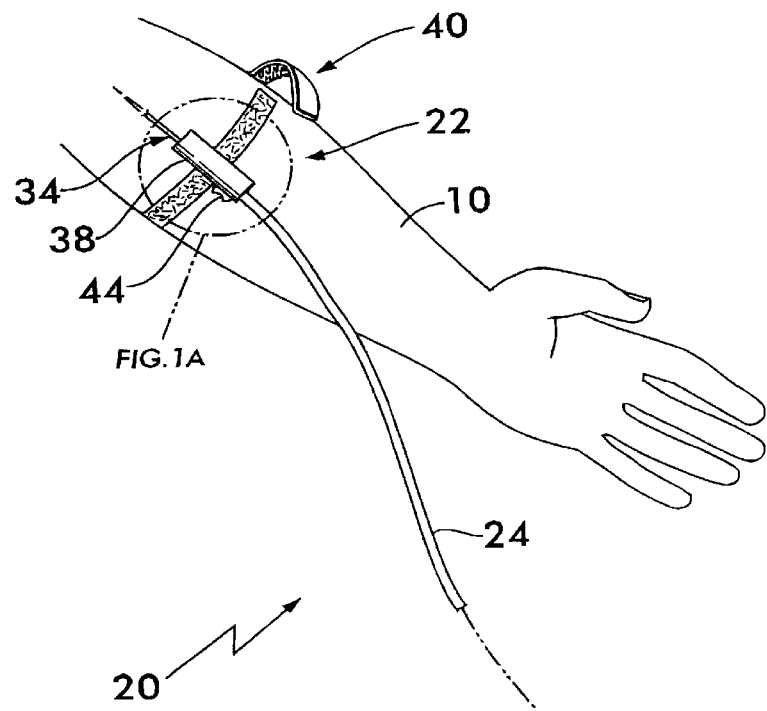
FIG. 1 is a diagrammatic view of the blood letting system of the present invention coupled to a blood vessel of a human being at one end and including a blood collecting portion at another end before blood letting has begun.
Figure 1:
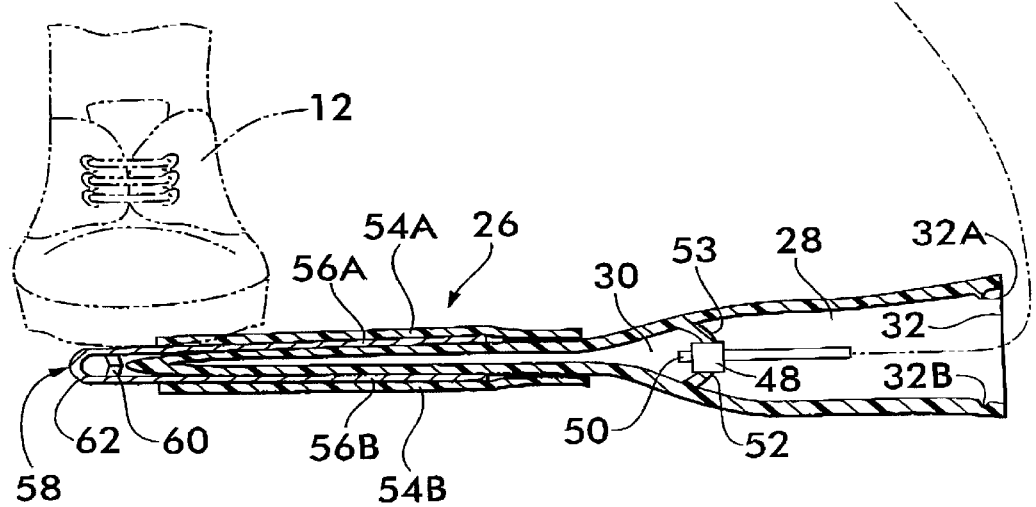

Referring now in detail to the various figures of the drawing wherein like reference characters refer to like parts, there is shown at 20 a non-biohazard blood letting system, 20 hereinafter "the system 20." The system 20 is a self-contained system that allows a patient, or a technician to assist a patient, to blood let safely and automatically. The system 20 basically comprises an intubation portion 22, a blood conveyor 24 and a blood collector 26.

The intubation portion 22 basically comprises a safety needle 34 having a safety cap 36 (FIG. 3). The safety needle 34 is coupled in fluid communication with the blood conveyor 24 via a housing 38. The housing 38 is affixed to an attachment strap 40 that aids in holding the safety needle 34 in place once inserted into a blood vessel. The strap may include a hook/pile 42 (e.g., the fastener sold under the mark VELCRO®) configuration for permitting the strap 40 to be releasably secured to the limb of the living being. The housing 38 may also comprise, although not required, a manually-operable clamp 44 that the patient can use to control the flow of blood, as will be discussed later.

Figure 1A:
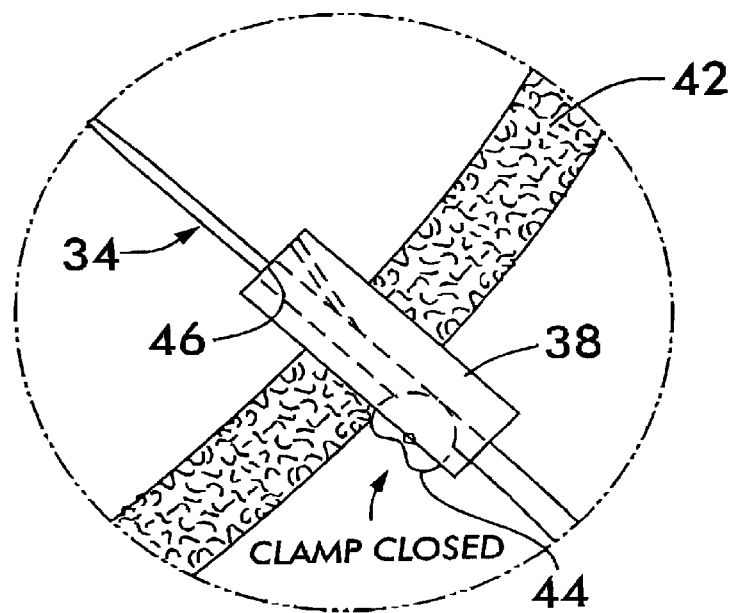
FIG. 1A is an enlarged view of the portion indicated in FIG. 1.
Figure 2A:
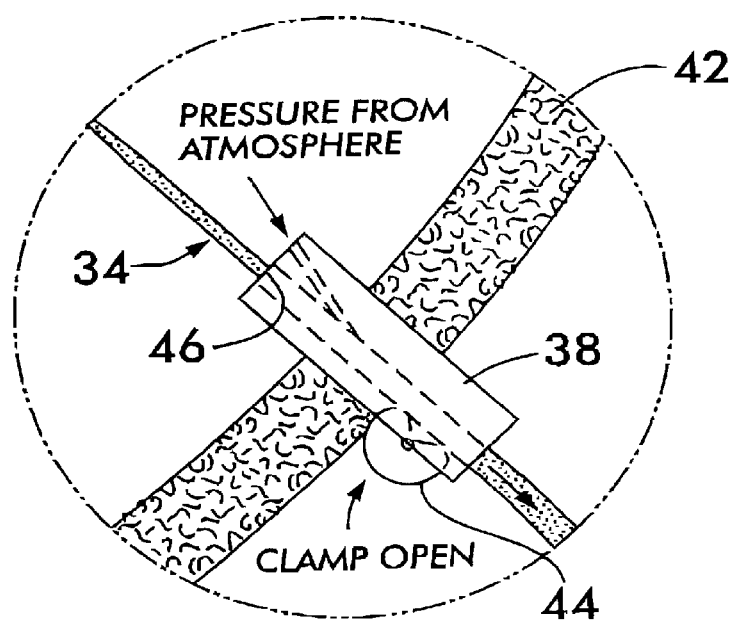
FIG. 2A is an enlarged view of the portion indicated in FIG. 2.
Figure 2:
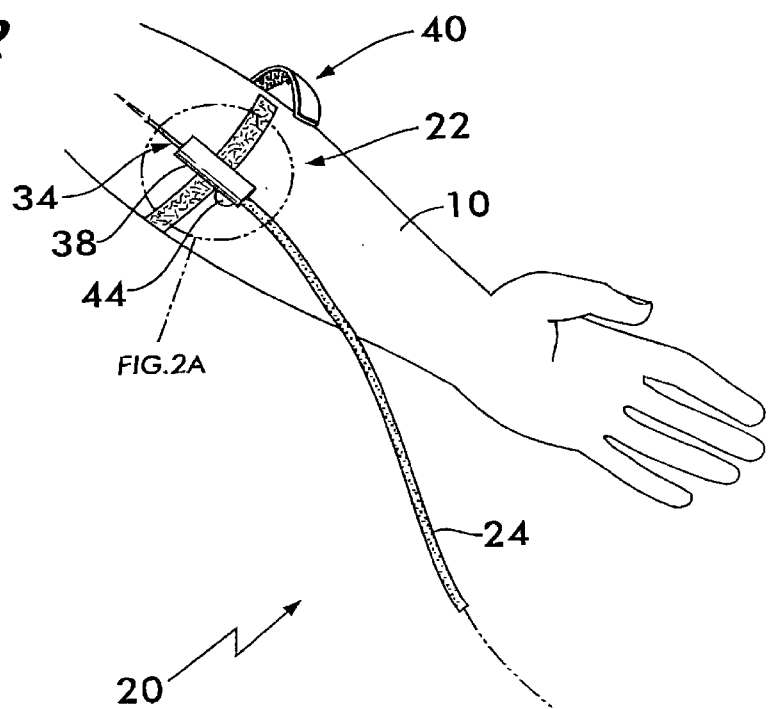
FIG. 2 is a cross-sectional view of a blood collector of the blood letting system of the present invention during blood letting showing the automatic removal of the blood from the human being to the blood collecting portion.
Figure 2:
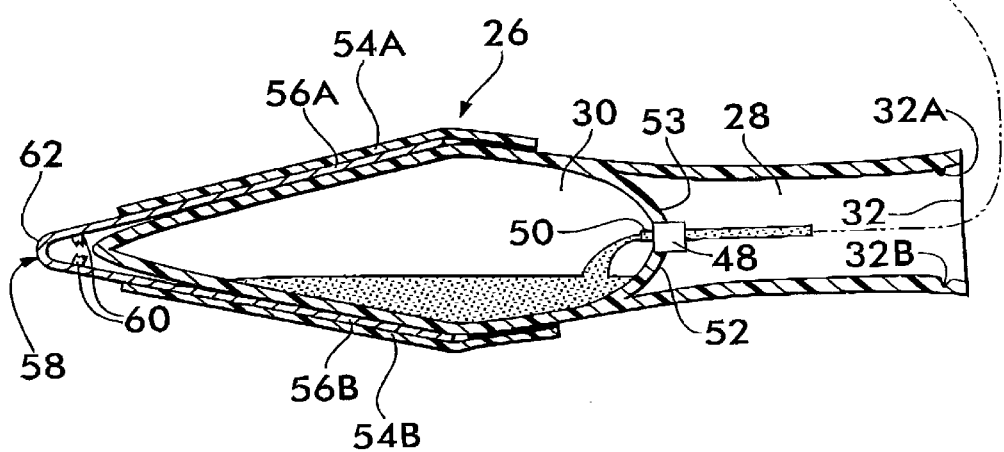

The blood conveyor 24 (e.g., a catheter, a pliable tube or any equivalent structure that can convey a fluid therein and that is pliable so that it can be stowed inside a bag or other similar structure ) is coupled at a first end 46 (FIG. 1A) to the safety needle 34 and to a one-way valve 48 adjacent its other end 50 (FIG. 2).

The blood collector 26 comprises two compartments: a blood collecting portion 30 and a resealable storage portion 28. These two compartments are isolated from each other via an inner wall 52 having an aperture 53 in which is disposed the one-way valve 48. The blood collecting portion 30 is formed by a durable material (e.g., plastic) having a memory that tends to maintain the blood collecting portion 30 in an expanded state (FIG. 2). An example of such a material is used in nose cleaners for infants, or other pliable bulbs used in medicine for creating a suction force (e.g., pipette pump, Cole-Parmer EW-24805-10 Pipette Filler).

On the exterior of the blood collecting portion 30 are a pair of molded pockets 54A and 54B on opposite sides of the blood collecting portion 30. These molded pockets 54A/54B form sleeves into which the free ends 56A and 56B of an expandor, e.g., a leaf spring 58, are captured. In particular, the leaf spring 58 may comprise a bent piece of spring steel having a memory or bias (which tends to move the free ends 56A/56B away from each other) and which is placed into a closed state (FIG. 1) at the factory whereby the free ends 56A and 56B are relatively close to each other. To hold this leaf spring 58 in the closed state, a frangible link 60 is also formed at the joined side 62 of the leaf spring 58, at the factory. With the leaf spring 58 in the closed state, the free ends 56A/56B are positioned in their respective sleeves 54A/54B, resulting in the joined side 62 of the leaf spring 58 being exposed, or otherwise protruding away from the blood collecting portion 30. As will be discussed in detail later, when an abrupt force is applied to the joined side 62, the frangible link 60 breaks, thereby allowing the leak spring 58 to immediately open so that the free ends 56A and 56B move away from each other rapidly, thereby causing the respective pockets 54A and 54B to also move away from each other, resulting in the rapid expansion of the blood collecting portion 30.

In addition, the interior of the blood collecting portion 30 comprises a micro-biological inactivating agent(s) (MBIA) which kill any micro-organisms, viruses, bacteria or the like to render any blood collected therein (as will be discussed in detail later) non-biohazardous; such agents may include bromine, chlorine, Methylene blue (MB) and its derivatives azure A, B, C and thionine. The inclusion of this agent, and/or other such agents, in the blood collecting portion 30 can be accomplished in several ways such as coating the interior surface of the blood collecting portion 30 with a coating of the MBIA; or, the material forming the blood collecting portion 30 may itself be formed of an MBIA; or, a tablet of bromine, or chlorine, etc., may be pre-disposed in the blood collecting portion 30 at the factory. In any case, the presence of the MBIA in the blood collecting portion 30 renders the collected blood non-biohazardous, thereby permitting the blood collector 26 to be discarded in a normal fashion.

The resealable storage portion 28 comprises the same material as the blood collecting portion 30. The safety needle 34 (along with the cap 36), the blood conveyor 24, the housing 38, the attachment strap 40 (also referred to as the "contents") are originally stored in this portion 28 at the factory and then the opening 32 is releasably sealed using, for example, a tongue 32A and groove 32B (also known as "pressure interlocking releasable rib and groove element closure"). When the patient or technician is ready to use the system 20, the releasable seal is opened, e.g., the tongue 32A is removed from the groove 32B and the contents are pulled out. When the blood letting is completed, the original contents are stored back into the resealable storage portion 28 and the releasable seal is closed, e.g., the tongue 32A is friction fitted into the groove 32B. The resealable storage portion 28 also contains a MBIA(s) therein so that once the blood letting is complete, should any blood still in the blood conveyor 24, or even in the needle 34 or in the housing 38 leak out, such leaking blood is also rendered non-biohazardous. Like the blood collecting portion 30, there are many ways to include the MBIA in the releasable storage portion 28. Once the blood letting is completed, the entire "used" system 20 can be disposed of in a conventional manner.

At the factory, the MBIA is disposed inside both the blood collecting portion 30 and the resealable storage portion 28 or, as discussed earlier, or is otherwise present inside both of these portions 28/30. Next, a vacuum is applied to the aperture 53 to cause the blood collecting portion 30 to deflate and assume a substantially flat state, as shown in FIG. 1. Then, the one way valve 48 is positioned in the aperture 53, thereby maintaining the vacuum within the blood collecting portion 30. Next, while in. the closed state, the free ends 56A/56B of the leaf spring 58 are positioned in their respective pockets 54A/54B, as shown in FIG. 1. Finally, the contents (e.g., the safety needle 34 (along with the cap 36), the blood conveyor 24, the housing 38, the attachment strap 40) are placed inside the resealable storage portion 28 and the opening 32 is closed using the releasable seal (e.g., the tongue 32A/groove 32B). Thus, except for any packaging, the system 20 is ready for shipment to end users.

Upon receipt of the system 20, the patient or technician opens the releasable seal and removes the contents through the opening 32. The blood collector 26 may be placed on the ground, or some other lower level with respect to the patient, to have gravity assist in the withdrawal of blood; however, it should be understood that this placement is not required. The patient or technician (hereinafter, "the patient") then operates the intubation portion 22 as follows: If the intubation portion 22 includes the manually-operable clamp 44, the clamp 44 is placed in the closed position (FIG. 1A). The cap 36 is removed and the safety needle 34 is coupled to a blood vessel of the patient, e.g., a vein in the arm 10 of the patient. Once intubation is completed, the patient then wraps the attachment strap 40 properly around the arm 10 to secure the needle 34 in place.

The patient then activates the system 20 by applying an abrupt force to the joined side 62 of the leaf spring 58; e.g., the patient can step strongly on the joined side 62 using his/her foot 12. This action fractures the frangible link 60 of the leaf spring 58, which causes the free ends 56A/56B of the leaf spring 58 to move away from each other suddenly. This movement causes the blood collecting portion 30 to expand suddenly, (FIG. 2), thereby creating a suction force to automatically draw a predetermined amount of blood 64 (e.g., approximately 550 cc or a pint) from the patient into the blood collecting portion 30. Before the actual drawing begins, the patient needs to open the clamp 44 (FIG. 2A, if the clamp 44 is present) at which time the blood in the blood vessel is exposed to the suction force from expanding blood collecting portion 30 which draws out the blood.

The one-way valve 48 permits only the flow of blood from the blood conveyor 24 into the blood collecting portion 30. There is no flow permitted from the blood collecting portion 30 into the blood conveyor 24, thereby preventing any possibility of air or other gas making its way toward the blood vessel. Furthermore, the protruding or exposed joined side 62 of the leaf spring 58 permits the abrupt force to be applied to the expandor (e.g., leaf spring 58) only, rather than to the blood collecting portion 30 which could rupture if the abrupt force were applied thereto.

It should be further noted, where the manually-operable clamp 44 is not present in the system 20, the activation of the system 20 would begin as soon as the abrupt force is applied to the joined side 62 of the leaf spring 58.

Given the characteristics of the expandor 58 and the material of the blood receiving portion 30, the system 20 generates the appropriate suction force for automatically drawing out the predetermined amount of blood (e.g., approximately 550 cc or a pint). Once the suction force is diminished and the predetermined amount of blood 64 is collected, the patient closes the clamp 44 (FIG. 1) and then disengages the intubation portion 22 by loosening the attachment strap 40, removing the needle 34 and restoring the cap 36 onto the needle which renders the needle 34 unusable. Next, the intubation portion 22 and the blood conveyor 24 are placed into the resealable storage portion 28 and the opening 32 is closed using the releasable seal, as shown in FIG. 3. The entire system 20 is now ready for safe disposal since all of the blood present in the blood collector 26 is rendered non-biohazardous due to the presence of the MBIA inside the blood collecting portion 30 and in the resealable storage portion 28.

Without further elaboration, the foregoing will so fully illustrate my invention that others may, by applying current or future knowledge, readily adopt the same for use under various conditions of service.

I claim:

1. An apparatus for permitting automatic, self-blood letting of a living being of a predetermined amount of blood and which renders the removed blood non-biohazardous for safe disposal, said apparatus comprising:

an intubator for coupling to a blood vessel of the living being;

a blood collector, said blood collector having an interior that contains a micro-biological inactivating agent; and a blood conveyor coupled between said intubator and said blood collector for passing blood from said intubator to said blood collector.

2. The apparatus of claim 1 wherein said blood collector comprises a first compartment formed of a material that tends to maintain said container in an expanded condition, said container being initially evacuated of any atmospheric pressure such that said container is substantially flat.

3. The apparatus of claim 2 wherein said first compartment comprises an expandor that is coupled to an exterior surface of said first compartment and having a pair of free ends, said expandor comprising a bias that tends to move said pair of free ends away from each other and wherein said expandor is initially positioned with said free ends closely adjacent each other.

4. The apparatus of claim 3 wherein said expandor comprises a frangible link that initially positions said free ends closely adjacent each other and which can be severed by applying an abrupt force to said frangible link.

5. The apparatus of claim 4 wherein each of one of said pair of free ends is positioned in a respective sleeve formed on opposite sides of the exterior of said container.

6. The apparatus of claim 5 wherein said expandor comprises a leaf spring having a first side having one of said pair of free ends and a second side having the other one of said pair of free ends and wherein said first side and said second side are coupled along a common edge, said frangible link being located adjacent said common edge and holding said first side and said second side together against said bias for positioning said free ends closely adjacent each other.

7. The apparatus of claim 6 wherein said common edge protrudes from the exterior of said container and to which an abrupt force is applied to sever said frangible link.

8. The apparatus of claim 2 wherein said blood collector further comprises a second compartment that can be opened or closed, said first and second compartments not being in fluid communication with one another and wherein said second compartment is used for storing said intubation portion and said blood conveyor when not in use.

9. The apparatus of claim 8 wherein said second compartment comprises a resealable opening.

10. The apparatus of claim 2 wherein said blood conveyor comprises a catheter having a first end in fluid communication with said intubator and having a second end that is in fluid communication with said first compartment via a one-way valve, said one-way valve permitting only the flow of blood from said blood conveyor to said first compartment.

11. The apparatus of claim 1 wherein said intubator is a safety needle.

12. The apparatus of claim 11 wherein said safety needle is coupled to a housing that can be releasably secured to a limb of the living being.

13. The apparatus of claim 12 wherein said housing comprises a releasable fastener.

14. The apparatus of claim 12 wherein said housing further comprises a manually-releasable clamp for controlling the removal of blood from the living being.

15. The apparatus of claim 1 wherein said microbiological inactivating agent kills any micro-organisms, viruses, bacteria or the like in blood removed from the living being.

16. The apparatus of claim 15 wherein said microbiological inactivating agent comprises the group consisting of bromine, chlorine, Methylene blue (MB) and its derivatives azure A, B, C and thionine.

17. The apparatus of claim 1 wherein said predetermined amount of blood is approximately 1 pint.

18. A method of permitting automatic, self-blood letting of a living being of a predetermined amount of blood while rendering the removed blood non-biohazardous for safe disposal, said method comprising:

(a) providing a blood collector that normally has an expanded state and which contains a micro-biological inactivating agent;

(b) evacuating said blood collector of atmospheric pressure to form a compressed state of said blood collector;

(c) coupling a releasable biasing member to said blood collector to maintain said blood collector in said compressed state until a desired time;

(d) coupling the blood vessel of the living being to said blood collector;

(e) activating said releasable biasing member to cause said blood collector to rapidly expand to draw said predetermined amount of blood into said blood collector;

(f) de-coupling the blood collector from the blood vessel; and (g) discarding said blood collector.

19. The method of claim 18 wherein said activating said releasable biasing member comprises applying an abrupt force to said releasable biasing member.

20. The method of claim 19 wherein said coupling of the blood vessel comprises:

(a) coupling a tube at one end to said blood collector;

(b) coupling the other end of said tube to a safety needle; and (c) intubating the living being by inserting said safety needle into the blood vessel of the living being.

21. The method of claim 20 wherein said coupling a tube at one end to said blood collector comprises coupling said one end through a one-way valve to said blood collector, said one-way valve permitting only the flow of blood from said tube into said blood collector.

22. The method of claim 21 further comprising providing a storage compartment with said blood collector, said storage compartment not being in fluid communication with said blood collector, said storage compartment holding said tube and safety needle before and after said self-blood letting.

23. The method of claim 22 wherein said providing a storage compartment further comprises including a microbiological inactivating agent within said storage compartment.

24. The method of claim 18 wherein said micro-biological inactivating agent kills any micro-organisms, viruses, bacteria or the like in the blood removed from the living being.

25. The method of claim 24 wherein said micro-biological inactivating agent comprises the group consisting of bromine, chlorine, Methylene blue (MB) and its derivatives azure A, B, C and thionine.

26. The method of claim 18 wherein said activating a releasable biasing member comprises:

(a) placing said blood collector on the ground; and (b) stepping strongly on a portion of said releasable biasing member.

27. The method of claim 18 wherein said predetermined amount of blood is approximately 1 pint.

28. The method of claim 20 wherein said coupling the blood vessel of the living being to said blood collector further comprises introducing a manually-operable clamp at said other end of said tube that is coupled to said safety needle, said manually-operable clamp being initially closed to prevent any passage of blood.

29. The method of claim 20 wherein said activating a releasable biasing member is further comprises opening said manually-operable clamp.

* * * * *